US010399849B2

(12) United States Patent
Thompson et al.

(10) Patent No.: US 10,399,849 B2
(45) Date of Patent: Sep. 3, 2019

(54) DEVICE AND METHOD FOR A THRESHOLD SENSOR (71) Applicant: INVENSENSE, INC., San Jose, CA (US)

(72) Inventors: Matthew Julian Thompson, Beaverton, OR (US); Stephen Lloyd, Los Altos, CA (US); Joseph Seeger, Menlo Park, CA (US)

(73) Assignee: INVENSENSE, INC., San Jose, CA (US)

(*) Notice: Subject to any disclaimer, the term of this patent is extended or adjusted under 35 U.S.C. 154(b) by 716 days.

(21) Appl. No.: 14/681,071

(22) Filed: Apr. 7, 2015

(65) Prior Publication Data

US 2016/0297670 A1    Oct. 13, 2016

(51) Int. Cl.
| | |
|---|---|
| B81B 7/00 | (2006.01) |
| H03K 21/02 | (2006.01) |
| B81B 7/02 | (2006.01) |
| B81C 99/00 | (2010.01) |
| H01L 21/66 | (2006.01) |
| G06F 11/30 | (2006.01) |

(52) U.S. Cl.
CPC .............. *B81B 7/0087* (2013.01); *B81B 7/02* (2013.01); *B81C 99/0045* (2013.01); *G06F 11/30* (2013.01); *H01L 22/34* (2013.01); *H03K 21/023* (2013.01)

(58) Field of Classification Search
CPC ...... B81B 7/0087; B81B 7/02; H03K 21/023; G06F 11/30; B81C 99/0045; H01L 22/34; G01L 5/00; G01P 15/04; G01P 15/06; H01H 35/14; H01H 35/146
USPC .................................. 73/865.8, 12.01–12.14
See application file for complete search history.

(56) References Cited

U.S. PATENT DOCUMENTS

| | | | |
|---|---|---|---|
| 6,321,654 B1 * | 11/2001 | Robinson | F42C 15/24 102/251 |
| 8,588,435 B2 * | 11/2013 | Bominaar-Silkens | H04R 3/002 381/150 |
| 9,316,550 B2 * | 4/2016 | Frangi | G01L 5/0052 |
| 2010/0083733 A1 * | 4/2010 | Russell | A42B 3/046 73/12.01 |
| 2015/0204904 A1 * | 7/2015 | Beyeler | G01D 5/12 324/750.25 |

* cited by examiner

*Primary Examiner* — Daniel S Larkin
*Assistant Examiner* — Anthony W Megna Fuentes
(74) *Attorney, Agent, or Firm* — Minisandram Law Firm; Raghunath S. Minisandram (57) ABSTRACT A device with a first MEMS device and a second MEMS device is disclosed. The first MEMS device is configured to sense at least one external influence. The second MEMS device is responsive to the at least one external influence. The first MEMS device is configured to change a state when the at least one external influence exceeds a threshold value. The first MEMS device is configured to retain the state below the threshold value, wherein the change in state of the first MEMS device is done passively and wherein the state of the first MEMS device is indicative of a status of the second MEMS device.

23 Claims, 10 Drawing Sheets

DEVICE AND METHOD FOR A THRESHOLD SENSOR

RELATED APPLICATION

None

TECHNICAL FIELD

The present invention relates generally to microelectromechanical systems (MEMS) device and more particularly, to one or more threshold sensors to sense external influence imparted to a MEMS device.

DESCRIPTION OF RELATED ART

MEMS devices are formed using various semiconductor manufacturing processes. MEMS devices may have fixed and movable portions. MEMS devices may include one or more MEMS sensors. MEMS sensors may sometimes be subjected to unwanted external influence. Sometimes, unwanted external influence may void the warranty, weaken the device, degrade the lifetime, damage the device or break the device. When diagnosing the MEMS device it is beneficial to know if the MEMS device was subjected to unwanted external influence.

With these needs in mind, the current disclosure arises. This brief summary has been provided so that the nature of the disclosure may be understood quickly. A more complete understanding of the disclosure can be obtained by reference to the following detailed description of the various embodiments thereof in connection with the attached drawings.

SUMMARY OF THE INVENTION

In one embodiment a device with a first MEMS device and a second MEMS device is disclosed. The first MEMS device is configured to sense at least one external influence. The second MEMS device is responsive to the at least one external influence. The first MEMS device is configured to change a state when the at least one external influence exceeds a threshold value. The first MEMS device is configured to retain the state below the threshold value. The change in state of the first MEMS device is done passively and the change in state of the first MEMS device is indicative of a status of the second MEMS device.

In another embodiment, a device with a first MEMS device and an object is disclosed. The first MEMS device is configured to sense at least one external influence. The object is responsive to the at least one external influence. The first MEMS device is configured to change a state when the at least one external influence exceeds a threshold value. The first MEMS device is configured to retain the state below the threshold value. The change in state of the first MEMS device is done passively and the change in state of the first MEMS device is indicative of a status of the object.

This brief summary is provided so that the nature of the disclosure may be understood quickly. A more complete understanding of the disclosure can be obtained by reference to the following detailed description of the preferred embodiments thereof in connection with the attached drawings.

BRIEF DESCRIPTION OF THE DRAWINGS

The foregoing and other features of several embodiments are described with reference to the drawings. In the drawings, the same components have the same reference numerals. The illustrated embodiments are intended to illustrate but not limit the invention. The drawings include the following Figures.

DETAILED DESCRIPTION

To facilitate an understanding of the adaptive aspects of the present disclosure, exemplary apparatus and method for sensing external influence upon a device is described. The specific construction and operation of the adaptive aspects of the apparatus and method for sensing external influence upon the device of the present disclosure are described with reference to an exemplary device with a first MEMS device and a second MEMS device.

Figure 1:
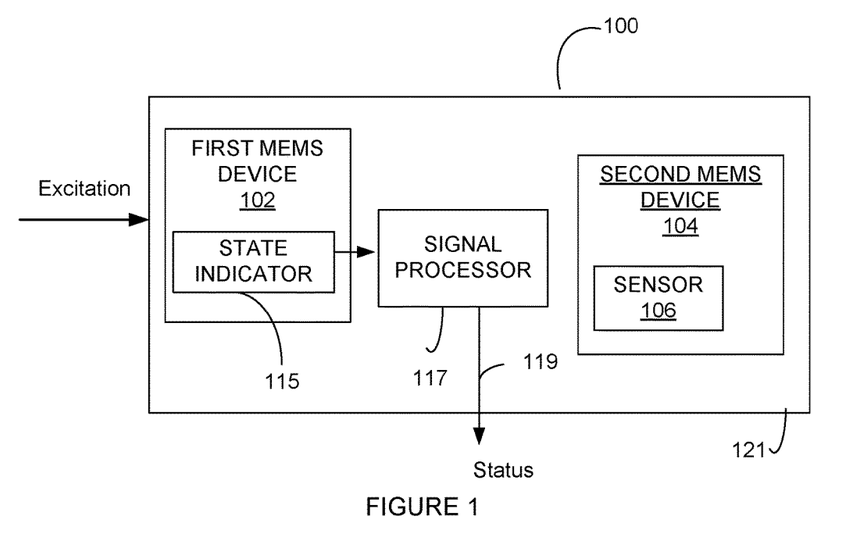
FIG. 1 shows a device with a first MEMS device and a second MEMS device, according to one aspect of the present disclosure.

FIG. 1 shows a device 100, with a first MEMS device 102 and a second MEMS device 104. In one example, the first MEMS device 102 may be configured to change state of a state indicator 115 when the external influence exceeds one or more threshold limits. Various adaptive aspects of the first MEMS device 102 will be later described in detail. The Second MEMS device 104 may be configured to have one or more sensor 106. The sensor 106 may be configured as a gyroscope, accelerometer, magnetometer, barometer, microphone and the likes. The first MEMS device 102 is configured to selectively measure any external influence the sensor 106 of the second MEMS device 104 may be subjected to. In some examples, the external influence may be imparted during the life cycle of the device. In some examples, the external influence may be imparted during an assembly process of the device 100. In yet other examples, the external influence may be imparted during the transportation or storage of the device 100. In yet another example, the external influence may be imparted during the operation of the device 100, for example, in an appliance into which the device 100 is incorporated into. In some examples, the external influence may be a shock. In some examples, the external influence may be a strain. In some examples, the external influence may be a temperature.

The first MEMS device 102, is further configured to be a passive device where only the energy from the external influence is used to change and store a state in a state indicator 115 of the First MEMS device 102. The passive device requires no external power supply like a battery or the likes. The state of the first MEMS device may be determined by visually looking at the device through a microscope like Infra-red, optical or other. The first MEMS device could also be coupled to a signal processor 117. The signal processor 117 may be configured to read the state indicator 115 of the first MEMS device 102 and output the status 119 that indicates the reliability of the second MEMS device 104. In another embodiment the first MEMS device 102, second MEMS device 104 and signal processor 117 may be anchored to a common surface or substrate 121.

Figure 1A:
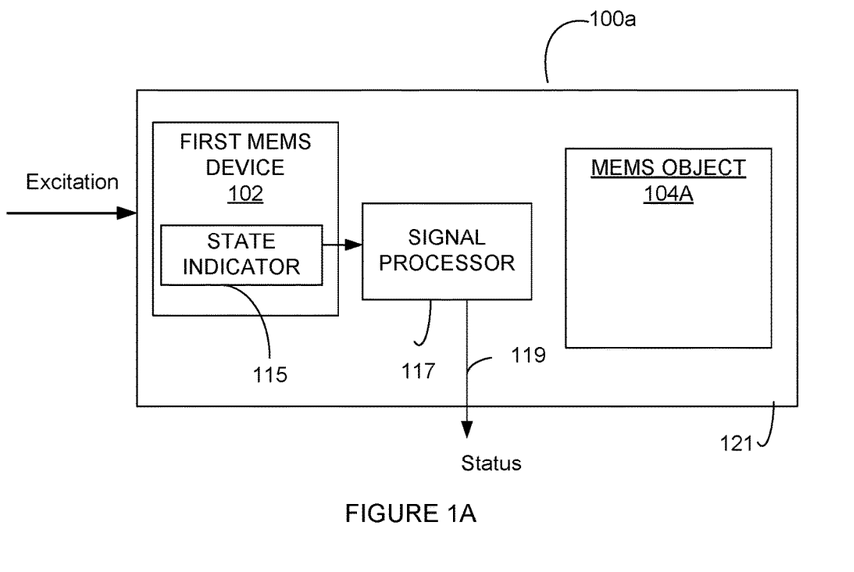
FIG. 1A shows a device with a first MEMS device and a MEMS object, according to one aspect of the present disclosure.

Now, referring to FIG. 1A, another device 100a is shown. The another device 100a is similar to device 100 shown in FIG. 1, except, instead of the second MEMS device 104, a MEMS object 104A is proviced. The MEMS object 104A is responsive to the at least one external influence.

Figure 2:
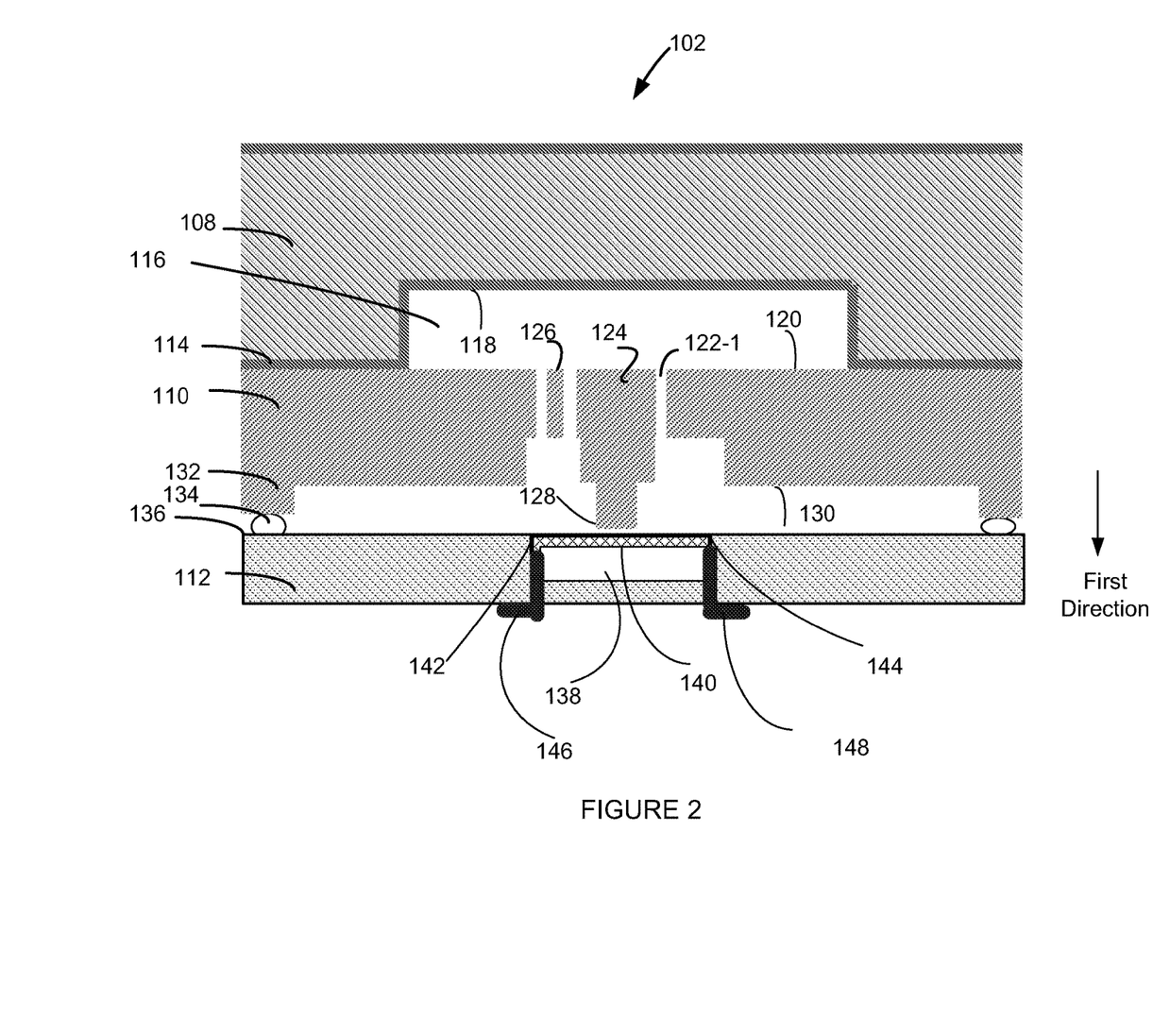
FIG. 2 shows an example first MEMS device, according another aspect of the present disclosure.

Now, referring to FIG. 2, an example first MEMS device 102 is described. The first MEMS device 102 includes a handle layer 108, a device layer 110 and a IC substrate 112. One or more threshold sensors are formed on the device layer 110. A fusion bond layer 114 bonds the handle layer 108 to device layer 110, to form an upper cavity 116, defined by the lower side 118 of the handle layer 108 and upper side 120 of the device layer 110.

FIG. 2 also shows trench pattern 122-1, a mass 124. The mass 124 is movable and is attached to a spring 126. The spring 126 is created by forming a plurality of trench patterns (not shown) on the device layer 110, for example, using a DRIE process. The mass 124 is configured to substantially move along a first direction. The mass 124 includes a plunger 128. In some examples, the plunger 128 may extend beyond the lower side 130 of the device layer 110.

The device layer 110 includes a standoff 132. The standoff 132 surrounds one or more threshold sensors formed on the device layer 110. A seal ring 134 is disposed between the standoff 132 and a top surface 136 of the IC substrate 112 so as to seal the threshold sensor of the first MEMS device 102.

The IC substrate 112 in some examples may be a CMOS substrate. The IC substrate 112 includes a substrate cavity 138. A first conductor 140 is disposed over the substrate cavity 138. The first conductor 140 is disposed relative to the plunger 128 such that upon sensing an external influence at or above a threshold value, for example, a force along the first direction at or above a threshold value, the plunger 128 will impact the first conductor 140 and break the first conductor 140. The first conductor 140 includes a first end 142 and a second end 144. The first end 142 is coupled to a first terminal 146 and the second end 144 is coupled to a second terminal 148. The MEMS device 102 described in FIG. 2 is an example of a normally closed switch.

A low resistance between the first terminal 146 and the second terminal 148 is indicative that the first conductor 140 is not broken. In other words, the device 100 has not experienced an external influence, in this example, a force substantially along the first direction above a threshold value. In some examples, this may be indicative of a first status of the second MEMS device 104. A high resistance between the first terminal 146 and the second terminal 148 is indicative that the first conductor 140 is broken. In other words, it is indicative that the device 100 has experienced an external influence, in this example, a force substantially along the first direction above a threshold value. In some examples, this may be indicative of a second status of the second MEMS device 104. In some examples, the second status may indicate that the second MEMS device 104 may have suffered damage which may render the second MEMS device 104 to not perform at its optimum performance level. In yet other examples, the second status may indicate that the second MEMS device 104 is inoperative due to the external influence above the threshold value.

One or more electronic circuits (not shown) may be disposed over the IC substrate 112 and the first terminal 146 and the second terminal 148 may be configured to electrically couple to the electronic circuit. In some examples, the resistance of the first conductor 140 is selectively measured on demand so that minimal energy (or power) is expended to measure the status of the first conductor 140 as to whether the first conductor 140 is broken or not. In other words, no energy (or power) is expended to operate the first MEMS device 102 and minimal energy (or power) is selectively expended to measure the status of the first conductor 140.

In the above example as described with reference to FIG. 2, the mass 124 and the plunger 128 is configured to move normal to the device layer 110 and the first conductor 140 is formed on the substrate 112. In some examples, the mass 124 and the plunger 128 may be configured move in-plane relative to the device layer 110 and the first conductor 140 may be formed on the device layer 110, instead on the substrate 112. In such an example, the plunger 128 is configured to move due to an excitation in a direction that is in-plane with the device layer. The first conductor 140 is disposed relative to the plunger 128 such that upon sensing an external influence at or above a threshold value, for example, a force along a direction in-plane relative to the device layer 110, at or above a threshold value, the plunger 128 will impact the first conductor 140 and break the first conductor 140. A pair of conductors may be disposed on the device layer coupled to a distal end of the first conductor 140 to permit measurement of a resistance of the first conductor 140. As previously discussed, a change in a resistance of the first conductor 140 may indicate a change in a status of the second MEMS device 104.

Figure 3:
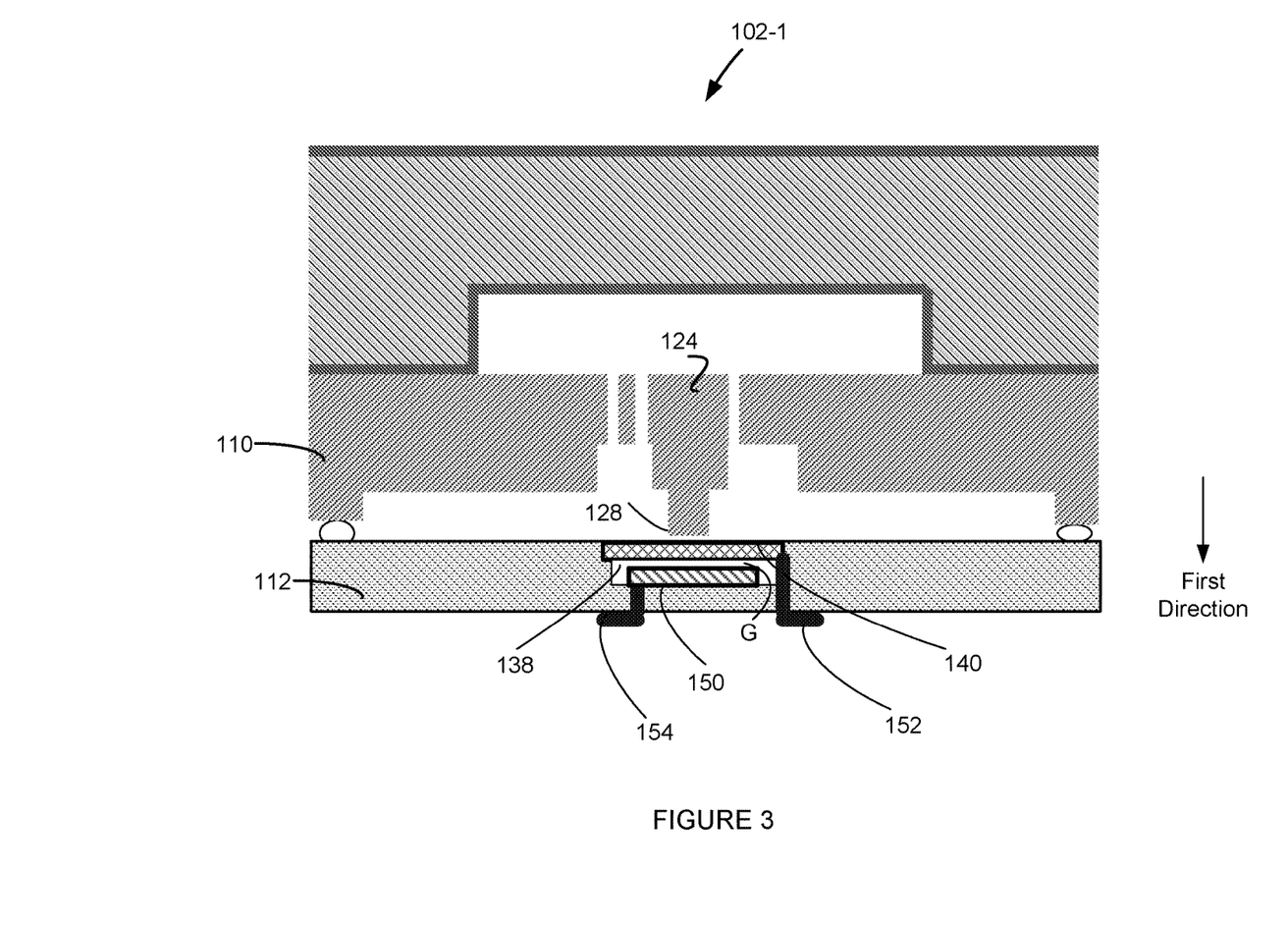
FIG. 3 shows another example first MEMS device, according to yet another aspect of the present disclosure.

Now referring to FIG. 3, another example first MEMS device 102-1 is described. In this example, the first MEMS device 102-1 is similar to the first MEMS device 102 in that the IC substrate 112 includes a substrate cavity 138 and the first conductor. However, in this example, a second conductor 150 is disposed in the substrate cavity 138. The second conductor 150 is disposed relative to the first conductor 140 so as to define a gap G. The plunger 128, the first conductor 140 and the second conductor 150 are disposed relative to each other such that upon sensing an external influence, for example, a force along the first direction, the gap G reduces. And, at or above a threshold value, the plunger impacts the first conductor 140 and the first conductor 140 couples to the second conductor 150. In one example, a third terminal 152 is coupled to the first conductor 140 and a fourth terminal 154 is coupled to the second conductor 150. The MEMS device 102-1 describe in FIG. 3 is an example of a normally open switch.

In one example, the first conductor 140 and the second conductor 150 form electrodes of a capacitor and a change in the gap G changes a capacitance value of the capacitor so formed. As the gap G reduces, the capacitance value of the capacitor reduces. This change in capacitance due to change in the gap G, in one example, may indicate a corresponding value of the external influence imparted to the first conductor 140. At or above a threshold value, the first conductor 140 couples to the second conductor 150, thereby reducing the gap G to zero, which will indicate a substantially zero capacitance value.

In another example, a high resistance between the third terminal 152 and the fourth terminal 154 is indicative that the first conductor 140 has not been moved by the plunger 128 to couple to the second conductor 150. In other words, the device 100 has not experienced an external influence, in this example, a force substantially along the first direction above a threshold value. In some examples, this may be indicative of a first status of the second MEMS device 104. A low resistance between the third terminal 152 and the fourth terminal 154 is indicative that the first conductor 140 has been moved by the plunger 128 to couple to the second conductor 150. In other words, it is indicative that the device 100 has experienced an external influence, in this example, a force substantially along the first direction above a threshold value. In some examples, this may be indicative of a second status of the second MEMS device 104. In some examples, the second status may indicate that the second MEMS device 104 may have suffered damage which may render the second MEMS device 104 to not perform at its optimum performance level. In yet other examples, the second status may indicate that the second MEMS device 104 is inoperative due to the external influence above the threshold value.

One or more electronic circuits (not shown) may be disposed over the IC substrate 112 and the third terminal 152 and the fourth terminal 154 may be configured to electrically couple to the electronic circuit. In some examples, the resistance between the third terminal 152 and the fourth terminal 154 is selectively measured on demand so that minimal energy (or power) is expended to measure the status of the first conductor 140 as to whether it has moved sufficiently to couple to the second conductor 150. In other words, no energy (or power) is expended to operate the first MEMS device 102 and minimal energy (or power) is selectively expended to measure the status of the first conductor 140.

In the above example as described with reference to FIG. 3, the mass 124 and the plunger 128 is configured to move normal to the device layer 110 and the first conductor 140 and second conductor 150 are formed on the substrate 112. In some examples, the mass 124 and the plunger 128 may be configured move in-plane relative to the device layer 110 and the first conductor 140 and second conductor 150 may be formed on the device layer 110, instead on the substrate 112. In such an example, the plunger 128 is configured to move due to an excitation in a direction that is in-plane with the device layer 110. The first conductor 140 is disposed relative to the plunger 128 such that upon sensing an external influence at or above a threshold value, for example, a force along a direction in-plane relative to the device layer 110, at or above a threshold value, the plunger 128 will impact the first conductor 140 and move the first conductor 140. A pair of conductors may be disposed on the device layer coupled to a distal end of the first conductor 140 and second conductor 150 so as to measure status of the second MEMS device 104, as previously described with reference to FIG. 3.

Figure 4:
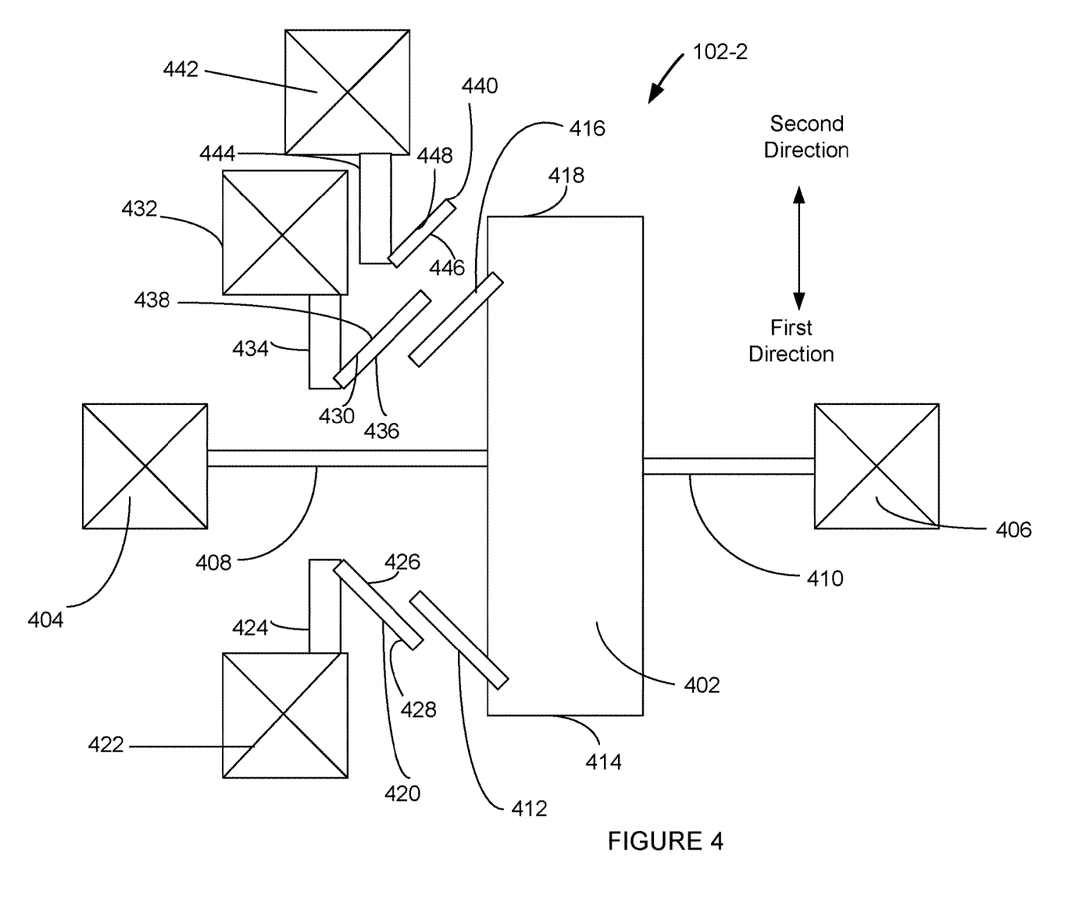
FIG. 4 shows yet another example first MEMS device, according to an aspect of the present disclosure.

Now, referring to FIG. 4, yet another example first MEMS device 102-2 is shown. In this example, a first mass 402 is movably coupled to a first anchor 404 and a second anchor 406. A first spring 408 couples the first mass 402 to the first anchor 404. A second spring 410 couples the first mass 402 to the second anchor 406. A first contact 412 is coupled to the first mass 402 and disposed about a first end 414 of the first mass 402. A second contact 416 is coupled to the first mass 402 and disposed about a second end 418 of the first mass 402. The first mass 402 is configured to move along a first direction and a second direction. A third contact 420 is disposed on a third anchor 422. For example, the third contact 420 may be disposed on a first arm 424 coupled to and extending from the third anchor 422. The third contact 420 is disposed relative to the first contact 412 such that when the first mass 402 moves sufficiently along the first direction, the first contact 412 slides over a first surface 426 of the third contact 420, slips over the third contact 420 and rests on a second surface 428 of the third contact 420. For example, the first contact 412 may be configured to slip over the third contact 420, when an external influence along the first direction is at or above a first threshold value. In some examples, the third contact 420 acts as a latch and holds the first contact 412 in place. In other words, the third contact 420 prevents the mass 402 from returning to its previous position once the external influence has exceeds a first threshold value.

A fourth contact 430 is disposed on a fourth anchor 432. For example, the fourth contact 430 may be disposed on a second arm 434 coupled to and extending from the fourth anchor 432. The fourth contact 430 is disposed relative to the second contact 416 such that when the first mass 402 moves sufficiently along the second direction, the second contact 416 slides over a third surface 436 of the fourth contact 430, slips over the fourth contact 430 and rests on a fourth surface 438 of the fourth contact 430. For example, the second contact 416 may be configured to slip over the fourth contact 430, when an external influence along the second direction is at or above a second threshold value. In some examples, the fourth contact 430 acts as a latch and holds the second contact 416 in place. In other words, the fourth contact 430 prevents the mass 402 from returning to its previous position once the external influence has exceeds a second threshold value. After the second contact has slipped over the fourth contact 430, fifth contact 440 comes into play.

The fifth contact 440 is disposed on a fifth anchor 442. For example, the fifth contact 440 may be disposed on a third arm 444 coupled to and extending from the fifth anchor 442. The fifth contact 440 is disposed relative to the second contact 416 such that after the second contact has slid over the fourth contact 430, an external influence at or above the third threshold value will cause the first mass 402 to move along the second direction. The movement of the first mass 402 causes the second contact 416 to slide over the fifth surface 446 of the fifth contact 440 and slides over the fifth contact 440 and rests on the sixth surface 448 of the fifth contact 440. For example, the second contact 416 may be configured to slip over the fifth contact 440, when an external influence along the second direction is at or above a third threshold value. In some examples, the fifth contact 440 acts as a latch and holds the second contact 416 in place. In other words, the fifth contact 440 prevents the mass 402 from returning to its previous position once the external influence has exceeds a third threshold value.

As one skilled in the art appreciates, the first MEMS device 102-2 in this example is configured to sense one threshold value, for example, first threshold value in the first direction and two threshold values, for example, second threshold value and third threshold value in the first directions. As one skilled in the art appreciates, the first MEMS device 102-2 may be configured to measure a plurality of threshold values in each direction, by appropriately configuring and positioning additional contacts that operatively work with the first contact and the second contact at different threshold values of the external influence.

In some examples, one or more terminals may be coupled to the first contact, second contact, third contact, fourth contact and the fifth contact to measure a resistance between the first contact and the third contact, second contact and the fourth contact and the second contact and the fifth contact. As an example, if the resistance between the first contact and the third contact is low, it indicates that the first MEMS device was subjected to an external influence at or above a first threshold value in the first direction. Similarly, if the resistance between the second contact and the fourth contact is low, it indicates that the first MEMS device was subjected to an external influence at or above a second threshold value in the second direction. Similarly, if the resistance between the second contact and the fifth contact is low, it indicates that the first MEMS device was subjected to an external influence at or above a third threshold value in the second direction.

As one skilled in the art appreciates, the first mass 402 may be appropriately doped to be conductive and may form a conductive path to measure the resistance between contacts discussed above. Similarly, first anchor 404, second anchor 406, third anchor 422, fourth anchor 432 and fifth anchor 442 may be appropriately doped to be conductive and may form a conductive path to measure the resistance between contacts discussed above.

Figure 5:
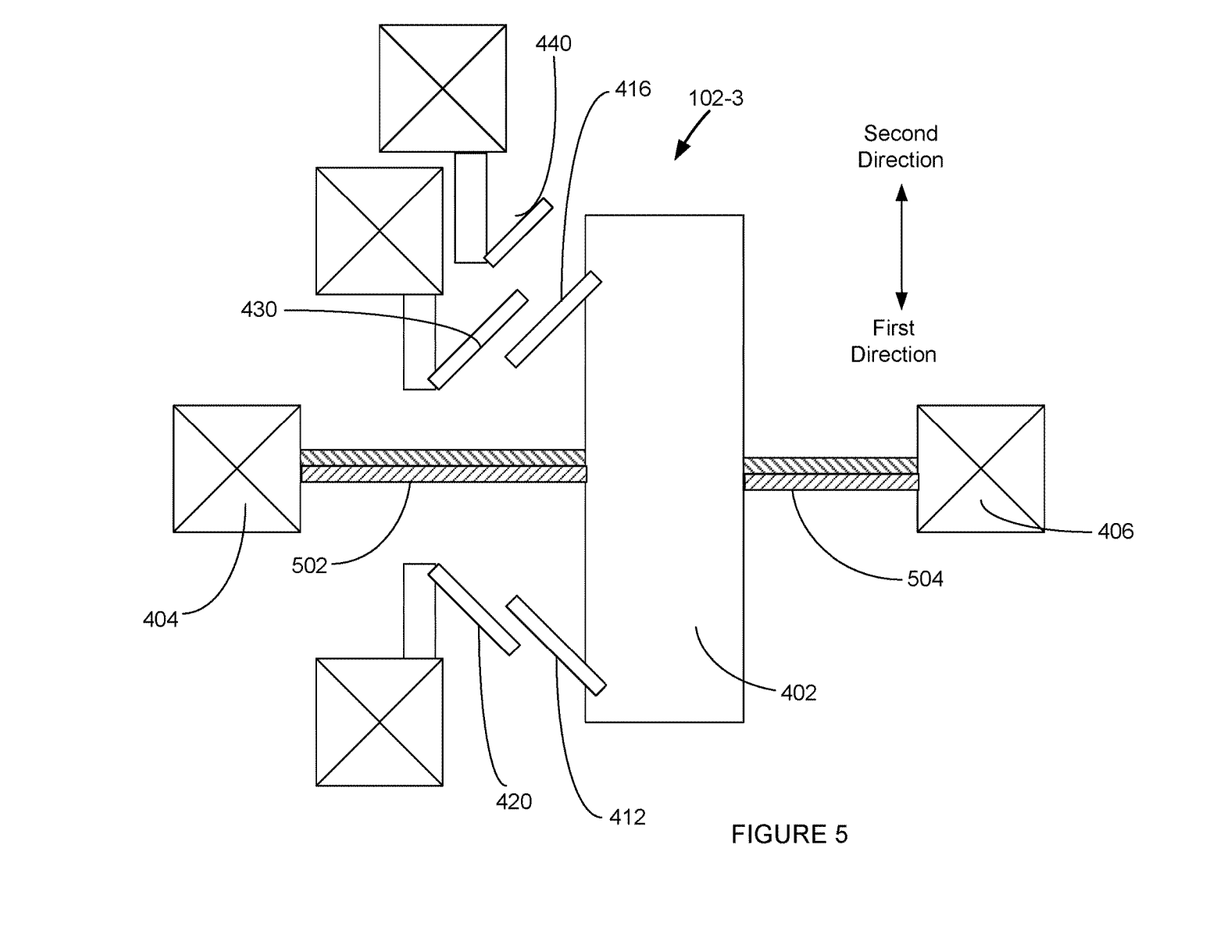
FIG. 5 shows yet another example first MEMS device, according to another aspect of the present disclosure.

Now, referring to FIG. 5, yet another example first MEMS device 102-3 is shown. The first MEMS device 102-3 of FIG. 5 is similar to the first MEMS device 102-2 of FIG. 4, except that a first thermal actuator 502 couples the first mass 402 to the first anchor 404. In some examples, the first thermal actuator 502 is a passive bimorph thermal actuator. And, a second thermal actuator 504 couples the first mass 402 to the second anchor 406. In some examples, the second thermal actuator 504 is a passive bimorph thermal actuator. The first thermal actuator 502 and the second thermal actuator 504 are configured such that when the first MEMS device 102-3 is subjected to a temperature lower than an ambient temperature, the first mass 402 moves in a direction substantially along the first direction. Further, the first thermal actuator 502 and the second thermal actuator 504 are configured such that when the first MEMS device 102-3 is subjected to a temperature higher than an ambient temperature, the first mass 402 moves in a direction substantially along the second direction. The first MEMS device is configured such that the first contact 412 slides over the third contact 420, when a temperature the first MEMS device is subjected to is above a first threshold value, in other words, when the temperature is at or below a certain value. Similarly, first MEMS device is configured such that the second contact 416 slides over the fourth contact 430, when a temperature the first MEMS device is subjected to is above a second threshold value. Further, the first MEMS device is configured such that the second contact 416 slides over the fifth contact 440, when a temperature the first MEMS device is subjected to is above a third threshold value.

As previously described with reference to FIG. 4, in some examples, the third contact 420 acts as a latch and holds the first contact 412 in place. In other words, the third contact 420 prevents the mass 402 from returning to its previous position, once the external influence has exceeded a preset threshold value. Similarly, fourth contact 430 and fifth contact 440 may act as a latch and hold the second contact 416 in place. In other words, the fourth contact 430 and fifth contact 440 prevent the mass 402 from returning to its previous position once the external influence has exceeded a preset threshold value.

Now, referring to FIGS. 6A-6D, an example friction spring configuration implementation for the contacts is described. The friction spring configuration for the contacts may be used in one or more example first MEMS device 102 previously described. Now, referring to FIG. 6A, the second mass 602 is movably coupled to a sixth anchor 604 by a third spring 606. The second mass 602 is configured to move along a third direction. The sixth contact 608 is movably coupled to the second mass 602 by a fourth spring 610. A seventh contact 612 is coupled to a seventh anchor 614. The sixth surface 616 of the sixth contact 608 is configured to touch and slide over a seventh surface 618 of the seventh contact 612, when the second mass 602 moves in the third direction.

Figure 6A:
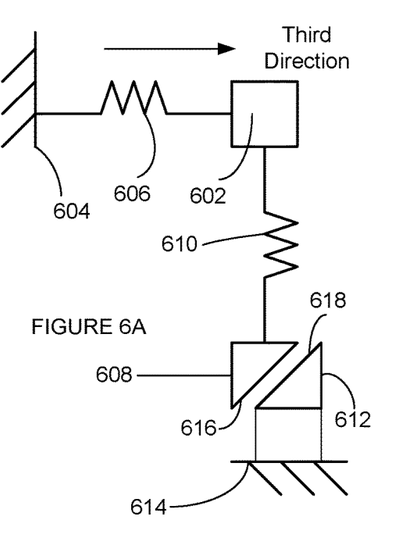
FIGS. 6A-6D show an example friction spring implementation of contacts for the first MEMS device, according to an aspect of the present disclosure.
Figure 6B:
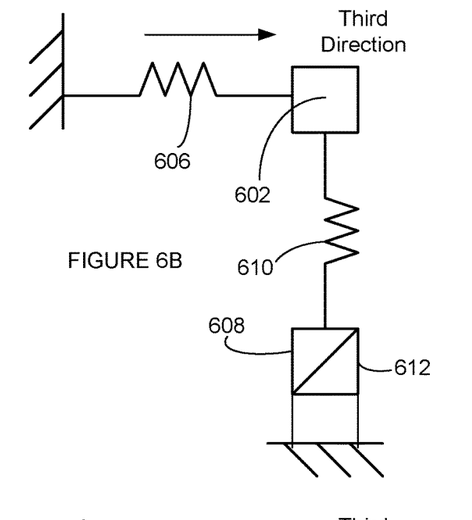

Now, referring to FIG. 6B, when an external influence, for example, a force is applied in the third direction, the third spring 606 expands and the second mass 602 moves in the direction of the third direction. As the second mass 602 continues to move due to the external influence, the sixth surface 616 of the sixth contact 608 comes in contact with the seventh surface 618 of the seventh contact 612.

Figure 6C:
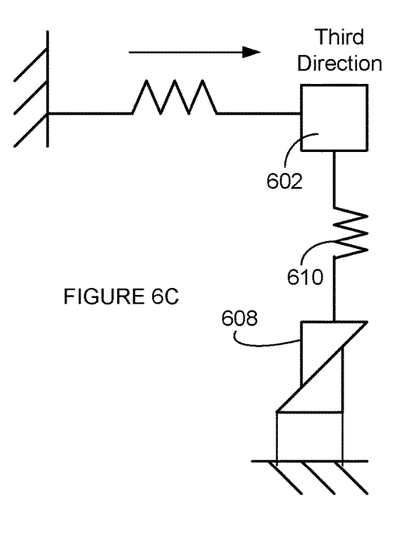
Figure 6D:
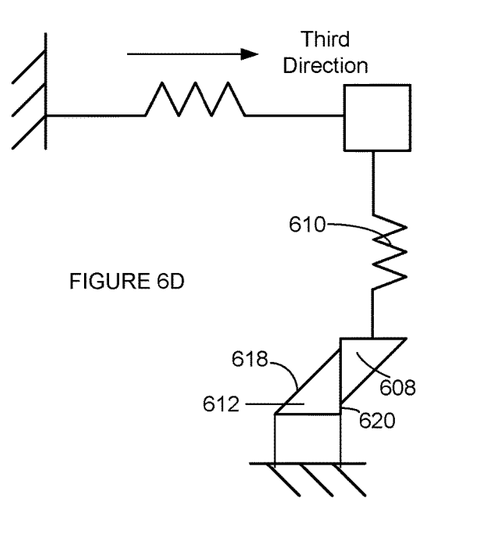

Now, referring to FIG. 6C, based on the extent of the external force, as the second mass 602 continues to move in the third direction, the sixth contact 608 continues to slide over the seventh contact 612 and the fourth spring 610 continues to contract. As sixth surface 616 slides over seventh surface 618 a friction force from the compression of spring 610 and the coefficient of friction of sixth surface 616 and seventh surface 618 opposes the motion. Now, referring to FIG. 6D, at a threshold value of the external influence, for example, a fourth threshold value, the sixth contact 608 completely slides over the seventh surface 618 of the seventh contact 612 and rests on the first side 620 of the seventh contact 612. The fourth spring 610 expands from its contracted position and holds the sixth contact 608 on the first side 620 of the seventh contact 612. A low resistance between the sixth contact 608 and the seventh contact 612 indicates that an external influence at or above the fourth threshold value was experienced. A high resistance between the sixth contact 608 and the seventh contact 612 indicates that an external influence at or above the fourth threshold value was not experienced. The strength of the spring 610, the geometry of sixth surface 616 and seventh surface 618 and the coefficient of friction of the sixth surface 616 and seventh surface 618 set the threshold limit of the switch. Once the device has reached position as shown in FIG. 6D a certain amount of work energy is required to reach this state. It is this work energy that sets the threshold limit. For example, a stiffness, shape and size of the friction surface and the spring determine a threshold value.

Now, referring to FIGS. 7A-7D another example friction spring configuration implementation describing the threshold contact operation is shown. The friction spring configuration for the contact may be used in one or more example first MEMS device 102 previously described. Now, referring to FIG. 7A, the third mass 702 is movably coupled to an eighth anchor 704 by a fifth spring 706. The third mass 702 is configured to move along a fourth direction. The eighth contact 708 is coupled to the third mass 702. In this example, the eighth contact 708 is configured to be compliant, for example, like a leaf spring. A ninth contact 712 is coupled to a ninth anchor 714. In this example, the ninth contact 712 is configured to be compliant, for example, like a leaf spring. The eighth surface 716 of the eighth contact 708 is configured to touch and slide over a ninth surface 718 of the ninth contact 712, when the third mass 702 moves in the fourth direction.

Figure 7A:
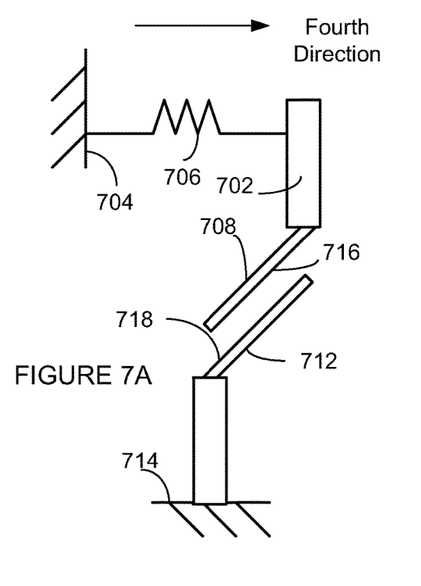
FIGS. 7A-7D show another example friction spring implementation of contacts for the first MEMS device, according to an aspect of the present disclosure.
Figure 7B:
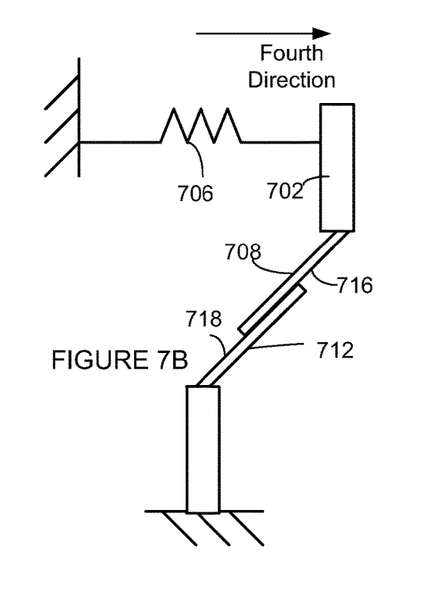

Now, referring to FIG. 7B, when an external influence, for example, a force is applied in the fourth direction, the fifth spring 706 expands and the third mass 702 moves in the direction of the fourth direction. As the third mass 702 continues to move due to the external influence, the eighth surface 716 of the eighth contact 708 comes in contact with the ninth surface 718 of the ninth contact 712.

Figure 7C:
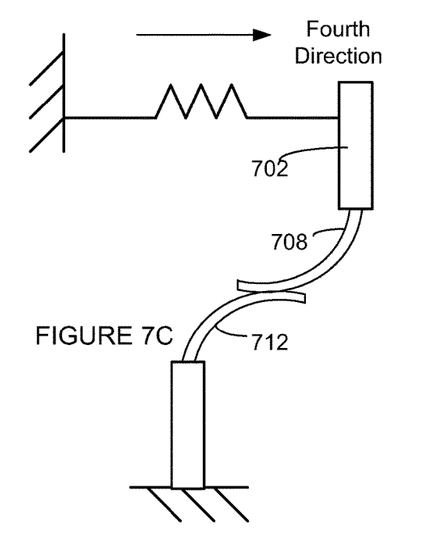
Figure 7D:
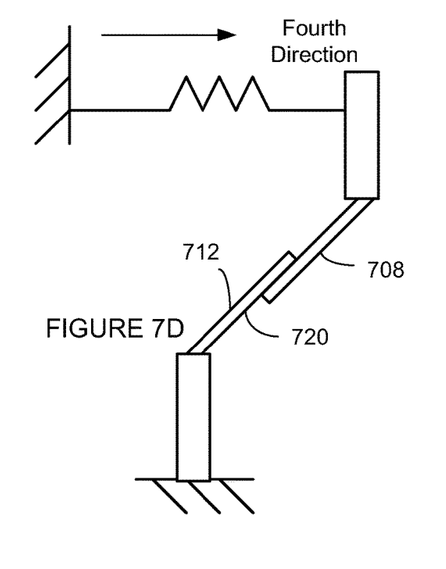

Now, referring to FIG. 7C, based on the extent of the external force, as the third mass 702 continues to move in the fourth direction, the eighth contact 708 continues to slide over the ninth contact 712, as both eighth contact 708 and the ninth contact 712 comply and bend to slide over each other. Now, referring to FIG. 7D, at a threshold value of the external influence, for example, a fifth threshold value, the eighth contact 708 completely slides over the ninth surface 718 of the ninth contact 712, as shown and rests on the first side 720 of the ninth contact 712. At this point, both the eighth contact 708 and ninth contact 712 have returned back to their original shape. The eighth contact 708 continued to rest on the first side 720 of the ninth contact 712. A low resistance between the eighth contact 708 and the ninth contact 712 indicates that an external influence at or above the fifth threshold value was experienced. A high resistance between the eighth contact 708 and the ninth contact 712 indicates that an external influence at or above the fifth threshold value was not experienced. The strength of the spring formed by the eighth contact 708 and ninth contact 712 and the geometry of the eighth surface 716 and ninth surface 718 set the threshold limit of the switch. Once the device has reached position as shown in FIG. 7D a certain amount of Work energy is required to reach this state. It is the Work energy that sets the threshold limit.

Figures 8A, 8B:
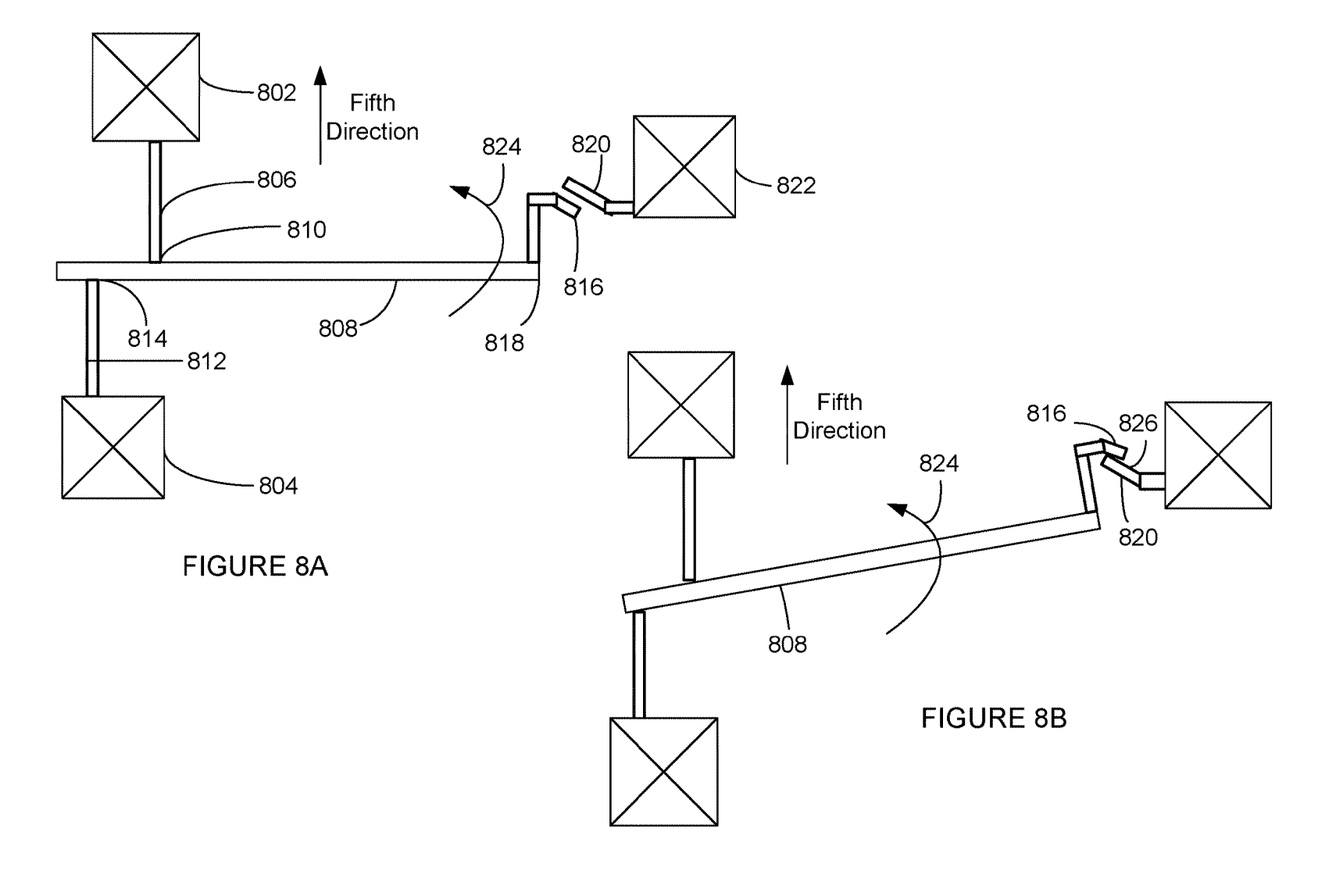
FIGS. 8A and 8B show an example strain gauge implementation of contacts for the first MEMS device, according to an aspect of the present disclosure.

Now, referring to FIGS. 8A and 8B, an example strain gauge configuration implementation for the contacts is described. The strain gauge configuration for the contacts may be used in one or more example first MEMS device 102 previously described. Now, referring to FIG. 8A, a tenth anchor 802 and an eleventh anchor 804 is provided. A first connector 806 couples the tenth anchor 802 to an arm 808 at a first location 810. A second connector 812 couples the eleventh anchor 804 to the arm 808 at a second location 814. A tenth contact 816 is disposed at a distal end 818 of the arm 808, away from the first location 810. An eleventh contact 820 is disposed in an operative relationship to the tenth contact 816 and coupled to a twelfth anchor 822.

The second location 814 is separated from the first location 810 by a distance so that when an external influence, for example, a strain is applied in the fifth direction, the tenth anchor 802 moves in the direction of the fifth direction and the eleventh anchor 804 moves (or pushed) in a direction opposite to the fifth direction, thereby rotating the arm 808 in a direction shown by the arrow 824. Now, referring to FIG. 8B, when an external influence greater than fifth threshold value is applied in the fifth direction, the arm 808 is sufficiently rotated along the direction shown by the arrow 824, wherein the tenth contact 816 goes past the eleventh contact 820 and rests on the upper side 826 of the eleventh contact 820. As one skilled in the art appreciates, the tenth contact 816 may be constructed such that the tenth contact 816 continues to rest on the upper side 826 of the eleventh contact 820 even when the external influence in the fifth direction is no longer present. A low resistance between the tenth contact 816 and the eleventh contact 820 indicates that an external influence at or above the fifth threshold value was experienced. A high resistance between the tenth contact 816 and the eleventh contact 820 indicates that an external influence at or above the fifth threshold value was not experienced.

Figure 9:
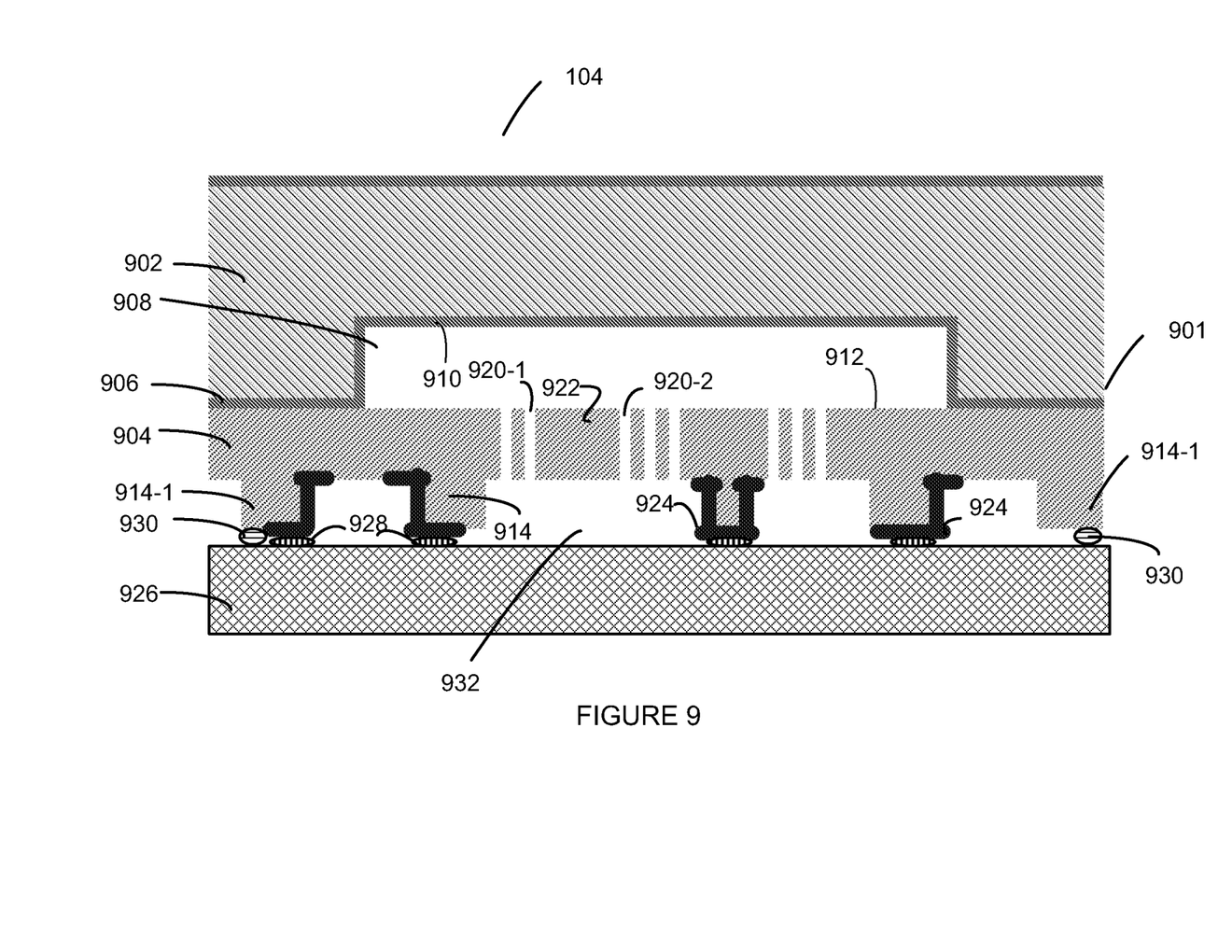
FIG. 9 shows an example second MEMS device, according to an aspect of the present disclosure.

Now, referring to FIG. 9 an exemplary second MEMS device 104 is described. Second MEMS device 104 includes a MEMS substrate 901 and integrated circuit substrate 926. MEMS substrate 901 includes a handle layer 902 and a device layer 904. A fusion bond layer 906 bonds the handle layer 902 to device layer 904, to form an upper cavity 908, defined by the lower side 910 of the handle layer 902 and upper side 912 of the device layer 904.

Now referring to device layer 904, a plurality of standoff 914 structures are formed on the device layer 904, for example, by deep reactive ion etching (DRIE) process. FIG. 9 further shows trench patterns 920-1 and 920-2, an actuator 922, device pads 924, integrated circuit substrate 926, IC pads 928 and seal ring 930. Seal ring 930 in some examples may be a conductive metal seal. A movable actuator 922 is created by forming a plurality of trench patterns 920-1 and 920-2 on the device layer 904, for example, using a DRIE process. Actuator 922 may be configured as a sensor, for example, to measure acceleration, angular rotation and the likes. Next, device pads 924, for example, made of germanium alloys are deposited and patterned on the device layer 904.

Integrated circuit substrate 926 includes one or more electronic circuits that communicate with various sensors formed on the device layer 904. IC pads 928, for example, made of aluminum alloys are deposited and patterned on the integrated circuit substrate 926. IC pads 928 are coupled to device pads 924 to provide a communication path to various sensors formed on the device layer 904. For example, device pads 924 may be conductively bonded with IC pads 928.

Standoff 914-1 surrounds various devices formed on the device layer 904. A seal ring 930 is formed on the standoff 914-1 to bond the device layer 904 with integrated circuit substrate 926, for example, to hermetically seal various devices formed on the device layer 904. Height of the standoff 914-1, along with seal ring 930 define height of the lower cavity 932.

As one skilled in the art appreciates, first MEMS device 102 may also be constructed as part of the second MEMS device 104. In one examples, a common handle layer may be used for first MEMS device 102 and second MEMS device 104. In some examples, elements of both first MEMS device 102 and second MEMS device 104 may be constructed on a common device layer. In yet other examples, the first MEMS device 102 and second MEMS device 104 may be constructed separately but packaged together in a device, for example, device 100.

Figure 10:
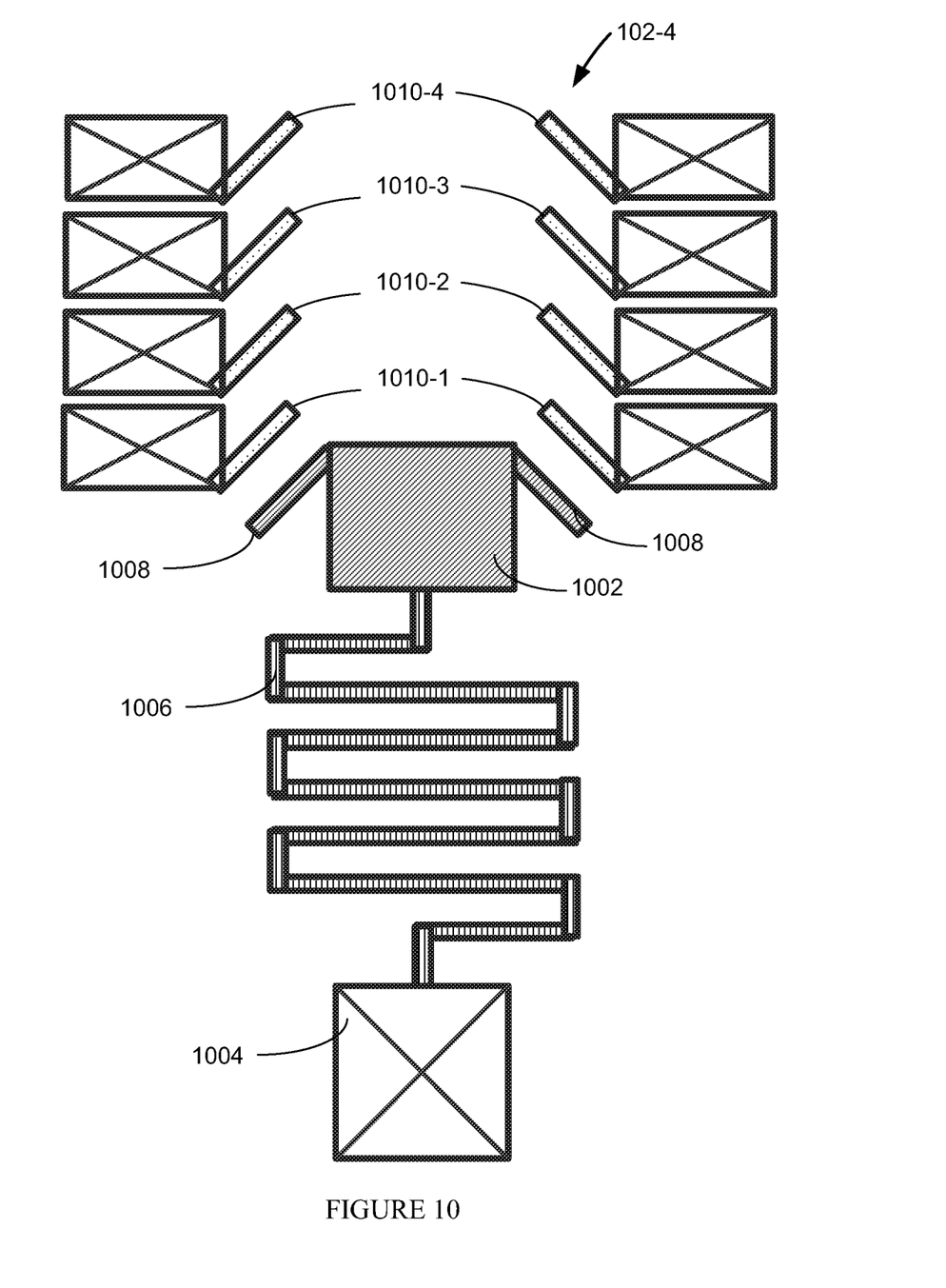
FIG. 10 shows an example first MEMS device configured as an event counter, according to one aspect of the present disclosure.

FIG. 10 shows another example first MEMS device 102-4. The first MEMS device 102-4 may be substantially similar to the first MEMS device 102-2, but reconfigured to be an event counter. MEMS device 102-4 has a movable mass 1002 connected to an anchor 1004 through a spring 1006. The movable mass 1002 further includes a contact 1008. A plurality of flexible latches 1010-1 to 1010-4 are disposed at substantially equal distance from the moveable mass 1002. Under an external excitation the contact 1008 of the moveable mass 1002 contacts the flexible latch and if the external influence exceeds a threshold the moveable mass moves past the flexible latch and the moveable mass 1002 is prevented from moving backwards. In this embodiment the stiffness of the flexible latch 1010-1 to 1010-4 is much greater than the stiffness of spring 1006 and therefore although the plurality of flexible latches 1001-1 to 1010-4 are disposed at different locations the threshold value is substantially the same. In this configuration the state of MEMS devices 102-4 represents the number of times the MEMS device 102-4 exceeds a single threshold value.

As one skilled in the art appreciates, although first MEMS device 102-4 has a pair of contacts 1008 and corresponding pairs of flexible latches 1010-1 to 1010-4, first MEMS device 102-4 may be modified to have a single contact and a plurality of single flexible latches.

As one skilled in the art appreciates, various examples of the first MEMS device described in this disclosure may be implemented in a single device that may be configured to measure threshold of different external influences. Further, various examples of the first MEMS device described in this disclosure may be implemented in a single device to measure different thresholds of the same external influence. Additionally, various examples of the first MEMS device described in this disclosure may be implemented in a single device to measure different thresholds of the same external influence in different directions.

While embodiments of the present invention are described above with respect to what is currently considered its preferred embodiments, it is to be understood that the invention is not limited to that described above. To the contrary, the invention is intended to cover various modifications and equivalent arrangements within the spirit and scope of the appended claims.

What is claimed is:

1. A device, comprising: a first MEMS device formed on a substrate, wherein the first MEMS device is configured to sense at least one external influence, and wherein the first MEMS device is configured to change a physical state and store the changed physical state when the at least one external influence exceeds a threshold value, and the first MEMS device is configured to retain the physical state below the threshold value, wherein the change in physical state of the first MEMS device is done passively, substantially due to an energy from the external influence, wherein the first MEMS device includes a device layer, the device layer including a mass movably coupled to the device layer, the mass including a plunger, wherein the mass including the plunger configured to move normal relative to the device layer; at least one conductor formed on a different layer and disposed relative to the plunger, wherein the plunger impacts one of the at least one conductor when the external influence exceeds the threshold value; and a second MEMS device formed on the substrate along with the first MEMS device, the second MEMS device responsive to the at least one external influence, wherein the stored physical state of the first MEMS device is indicative of a status of the second MEMS device.

2. The device of claim 1, wherein the external influence is at least one of shock, strain and temperature.

3. The device of claim 1, wherein the second MEMS device is at least one of a gyroscope, accelerometer, magnetometer, barometer and microphone.

4. The device of claim 1, wherein the change in state of the first MEMS device is irreversible.

5. The device of claim 1, wherein the state is indicative of the direction of the external influence.

6. The device of claim 1, wherein the stored physical state of the first MEMS device is detected visually, with a microscope.

7. The device of claim 1, further including a readout circuit to read the state of the first MEMS deice and output the status of the second MEMS device.

8. The device of claim 1, wherein the first MEMS device further comprises a normally closed mechanical switch that opens when the external influence exceeds the threshold value.

9. The device of claim 1, wherein elements of the second MEMS device are formed on the device layer.

10. The device of claim 9, wherein the plunger deforms the conductor when the external influence exceeds the threshold value and a capacitance between the conductor and another conductor determines the state, wherein capacitance is indicative that the external influence has exceeded the threshold value and another capacitance is indicative that the external influence has not exceed the threshold value.

11. The device of claim 1, wherein the first conductor is broken when the external influence exceeds the threshold value and the resistance of the conductor determines the state of the second MEMS device, wherein a resistance indicates that the external influence exceeded the threshold and another resistance indicates that the external influence did not exceed the threshold.

12. The device of claim 11, further including a signal processor, the signal processor anchored to the substrate with the first MEMS device and the second MEMS device and the signal processor configured to determine the resistance of the conductor and based on the determined resistance, output a signal indicative of the reliability of the second MEMS device.

13. A device, comprising: a first MEMS device formed on a substrate, wherein the first MEMS device is configured to sense at least one external influence, wherein the first MEMS device includes a device layer, the device layer including a mass movably coupled to the device layer, the mass including a plunger, wherein the mass including the plunger configured to move normal relative to the device layer; at least one conductor formed on a different layer and disposed relative to the plunger, wherein the plunger impacts one of the at least one conductor when the external influence exceeds the threshold value; and a MEMS object formed on the substrate along with the first MEMS device, wherein a status of the MEMS object selectively changes from a first status to a second status in response to the at least one external influence; wherein the first MEMS device is configured to change a physical state and store the changed physical state when the at least one external influence exceeds a threshold value, and the first MEMS device is configured to retain the physical state below the threshold value, wherein the change in physical state of the first MEMS device is done passively, substantially due to an energy from the external influence, and wherein the change in the physical state of the first MEMS device is indicative of the change in the status of the MEMS object from the first status to the second status.

14. The device of claim 13, wherein the external influence is at least one of shock, strain and temperature.

15. The device of claim 13, wherein the change in state of the first MEMS device is irreversible.

16. The device of claim 13, wherein the change in status is indicative of the direction of the external influence.

17. The device of claim 13, wherein the stored physical state of the first MEMS device is detected visually, with a microscope.

18. The device of claim 13, further including a readout circuit to read the state of the first MEMS device and output the status of the MEMS object.

19. The device of claim 13, wherein the first MEMS device further comprises a normally closed mechanical switch that opens when the external influence exceeds the threshold value.

20. The device of claim 13, wherein elements of the MEMS object are formed on the device layer.

21. The device of claim 20, wherein the plunger deforms the conductor when the external influence exceeds the threshold value and a capacitance between the conductor and another conductor determines the state, wherein capacitance is indicative that the external influence has exceeded the threshold value and another capacitance is indicative that the external influence has not exceed the threshold value.

22. The device of claim 13, wherein the first conductor is broken when the external influence exceeds the threshold value and the resistance of the conductor determines the status of the MEMS object, wherein a resistance indicated that the external influence exceeded the threshold and another resistance indicated that the external influence did not exceed the threshold.

23. The device of claim 22, further including a signal processor, the signal processor is anchored to the substrate with the first MEMS device and the MEMS object and the signal processor is configured to determine the resistance of the conductor and based on the determined resistance, output a signal indicative of the reliability of the MEMS object.

* * * * *